United States Patent [19]
Hardy et al.

[11] 3,935,235
[45] Jan. 27, 1976

[54] LACTONES

[75] Inventors: Francis R. F. Hardy, Chester; Ian Robert King, Luton, both of England

[73] Assignee: Laporte Industries Limited, Luton, England

[22] Filed: Apr. 8, 1974

[21] Appl. No.: 459,227

[30] Foreign Application Priority Data
Apr. 11, 1973 United Kingdom............... 17498/73

[52] U.S. Cl............................ 260/343.6; 260/526 N
[51] Int. Cl.²...................................... C07D 307/32
[58] Field of Search..................... 260/343.6, 526 N

[56] References Cited
UNITED STATES PATENTS

| | | |
|---|---|---|
| 2,876,258 | 3/1959 | Phillips et al.................. 260/526 N |
| 3,037,052 | 5/1962 | Bortnick............................ 260/343 |

OTHER PUBLICATIONS

Ansell et al., *Quarterly Reviews,* 1964, pp. 211–225, (1964).

*Primary Examiner*—Anton H. Sutto
*Assistant Examiner*—Jane S. Myers
*Attorney, Agent, or Firm*—Larson, Tayor & Hinds

[57] ABSTRACT

A feed material containing the group $-O-(CR_2)_n-CO-$ in a macrocyclic ring or acylic chain is heated to between 300°C and 500°C in the absence of a catalyst to give a mono-unsaturated acyclic carboxylic acid. For example polymeric ε-caprolactone gives δ-ε hexenoic acid. This acid is then cyclised by heating with a strong protonating agent. In the example the product is γ-caprolactone or 4-hexanolactone.

3 Claims, No Drawings

LACTONES

The present invention relates to the production of γ-lactones.

British Pat. No. 1 203 753 describes a method of making lactones wherein a material containing the group —O — $(CR_2)_n$—CO —, in which R represents a hydrogen atom or a methyl group and $n$ is an integer from 4 to 11, is heated to a temperature of at least 50°C in the presence of a metal salt of an organic acid having from 1 to 6 carbon atoms or a metal oxide, the metal being zinc, copper, calcium, strontium or barium. The method described is particularly applicable to the preparation of ε-caprolactone.

According to the present invention there is provided a process for the production of a γ-lactone which comprises (a) heating a feed material containing the group —O — $(CR_2)_n$—CO— in which R represents a hydrogen atom or a methyl group and n is an integer from 5 to 11 in a macrocyclic ring or an acyclic chain, to a temperature of from 300°C to 500°C in the absence of substantial amounts of added catalyst to form an acyclic carboxylic acid whose δ atom is unsaturated and (b) cyclising said acyclic carboxylic acid by contacting it with a catalyst comprising a strong protonating agent.

The starting material containing the group —O—$(CR_2)n$ —CO— in an acyclic chain may be formed as a by-product in the preparation of lactones from starting materials such as cyclic ketones and peracids. In the case where cyclohexanone and peracetic acid are reacted together to form ε- caprolactone one side product is a material which appears to contain the group —O— $(CH_2)_5$ —CO— in an acyclic chain. Various cyclic polymers may be present in such side product but they appear to revert to acyclic material on heating. It will be apparent that the said group is also present in homopolymerised lactones, e.g. macrocyclic polymers. The present invention is particularly suitable for converting such materials into γ- caprolactone.

It has now been found that if, for example, materials containing the group —O— $(CH_2)_5$ —CO— in an acyclic chain are heated in the substantial absence of added catalyst, then the main product is not ε-caprolactone but is the unsaturated acid, 5- hexenoic acid or δ - ε unsaturated hexanoic acid. The unsaturated acid may be formed in good yields. Preferably the material containing the acyclic chain is heated at atmosphere pressure and preferably at a temperature within the range of from 350°C to 500°C. Side products such as undesirable lactones or cyclopentanone may be formed but then may be removed by fractional distillation.

By the term "γ- lactone" is meant a lactone having a total of 4 carbon atoms in the lactone ring. An "acyclic carboxylic acid whose δ atom is unsaturated" means an acylic carboxylic acid which is unsaturated in the δ-ε or γ-δ position, i.e. an acid which has the part formula —C = C — C — C C — COOH or —C = C — C — C — C — COOH.

The strong protonating agent may be one or more of a strong acid such as sulphuric acid, toluene p-sulphonic acid, formic acid, oxalic acid or trifluoroacetic acid, a cation exchange resin in the free acid form, a strongly acidic mixture containing hydrogen ions such as hydrogen halides in acetic acid or a similar protonating agent. A preferred strong protonating agent is a cation exchange resin in the free acid form. The cation exchange resin is preferably a macro-reticular exchange resin such as that sold by Rohm and Haas as AMBERLYST 15. AMBERLYST is a registered Trade Mark.

According to another aspect of the present invention there is provided a process for the production of a γ-lactone which comprises cyclising an acyclic carboxylic acid in which an olefinic bond is present in the δ - ε position by contacting it with a cation exchange resin in the free acid form at a temperature of from 100°C to 200°C.

It will be understood from the above that the cyclising step may be carried out in the presence of γ- lactone. The unsaturated carboxylic acid is normally in the liquid phase and is conveniently contacted continuously in a column with the strong protonating agent which may be a liquid or a solid.

Preferably the temperature of the contacting is from 120°C to 160°C. The reaction with the strong protonating agent may result in a small amount of δ- lactone remaining or being formed and this may be removed from the γ- lactone by, for example, distillation and then recycled over the catalyst. Unreacted acid may also be recovered by distillation and recycled.

The present invention also provides γ- lactones wherever made according to the process of the present invention. The γ- lactones are particularly useful as solvents for certain polymeric materials such as polystyrene, cellulose butyrate acetate and polyurethane.

A specific embodiment of the present invention will now be described by way of example only.

EXAMPLE

A sample of polymeric residue (2001.1g) from the preparation of δ- caprolactone from cyclohexanone and peracetic acid containing the acyclic chain —O— $(CH_2)_5$ —CO—O— was heated in a flask with a distillation head and condenser attached. By the time the temperature has reached 300°C a distillate (95g), mainly water, had collected. Over the temperature range of from 360°C to 460°C, an organic distillate (1628.9g) was obtained and analysed at approximately 70% 5 - hexenoic acid, 25% δ- caprolactone and 5% cyclopentanone. The components of the distillate were separated by fractional distillation. The polymeric residue remaining was recycled.

The 5- hexenoic acid was fed to a column containing AMBERLYST 15 cation exchange resin in the H+ form (100 mls) at a rate of about 0.5 bed volumes per hour. The column was electrically heated and its temperature maintained at 140°C. The column effluent was analysed at γ- caprolactone 87%, δ- caprolactone 1% and 5 - hexenoic acid 11%.

The 5- hexenoic acid was recycled.

The ε- caprolactone from the first stage and the δ- caprolactone from the second stage were treated in accordance with out copending British patent application Ser. No. 17497/73 to give 5-hexenoic acid which was passed to the second stage of the process of this invention.

We claim:

1. A process for the production of a γ-caprolactone comprising (a) heating a polymeric feed material containing the group — O — $(CR_2)_5$ —CO —, in which R represents a hydrogen atom or a methyl group, in a macrocylic ring or an acyclic chain, to a temperature of from 300°C to 500°C in the absence of added catalyst thereby to form an acyclic carboxylic acid whose δ atom is unsaturated and (b) cyclising said acyclic carboxylic acid by contacting it with a catalyst comprising a strong protonating agent, selected from the group consisting of strong acids, cation exchange resins in the free acid form, and strongly acidic mixtures containing hydrogen ions.

2. The process according of claim 1, wherein the feed material, containing the group $-O-(CR_2)_5-CO-$ in an acyclic chain, has been formed as a by-product in the preparation of lactones from the reaction of cyclic ketones with peracids.

3. The process of claim 1, wherein the unsaturated acyclic carboxylic acid is in the liquid phase and is contacted continuously in a column with the strong protonating agent which is a solid, the cyclising being effected at a temperature in the range 120°C to 160°C.

* * * * *